United States Patent [19]
Szabo

[11] Patent Number: 5,474,748
[45] Date of Patent: Dec. 12, 1995

[54] WATER DECONTAMINATING DEVICE

[76] Inventor: Louis Szabo, 2940 Olafson Avenue, Richmond, B.C., Canada, V6X 2R3

[21] Appl. No.: 160,772

[22] Filed: Dec. 3, 1993

[51] Int. Cl.⁶ .............................. B01J 19/08; B01J 19/12; C02F 1/32; C02F 1/78
[52] U.S. Cl. ................. 422/186.04; 422/186.07; 422/186.09; 422/186.11; 422/186.18; 422/186.19; 422/907; 422/186.3
[58] Field of Search ............................ 422/186.3, 186.07, 422/186.04, 186.09, 186.11, 186.18, 186.19, 907

[56] References Cited

U.S. PATENT DOCUMENTS

| | | | |
|---|---|---|---|
| 4,141,830 | 2/1979 | Last | 210/632 |
| 4,156,652 | 5/1979 | Wiest | 250/527 |
| 4,179,616 | 12/1979 | Coviello et al. | 250/527 |
| 4,189,363 | 2/1980 | Bietzel | 204/157.1 R |
| 5,266,215 | 11/1993 | Engelhard | 210/748 |

OTHER PUBLICATIONS

Dimitriov, M. A., "Design Guidance Manual for Ozone Systems", Pan Am, Committee of the Intr'l Ozone Assn., 1990, pp. 3–55, 73–86.

*Primary Examiner*—Donald P. Walsh
*Assistant Examiner*—Daniel Jenkins

[57] ABSTRACT

A sterilizing apparatus is provided to simultaneously generate ozone and expose a contaminated fluid to ionizing radiation, such as UV radiation, for the sterilization of water. The device includes an air supply conduit to circulate current of air through an ozonation chamber, with the conduit being routed through a water exposure chamber, wherein the air is cooled by the relatively lower temperature of the water at the same time as the water is being decontaminated by exposure to sterilizing radiation. The conduit continues into the air exposure chamber, where it is positioned adjacent the UV lamp to dry the air by the warmth generated by the lamp. The second part may comprise a metal tube having a helical portion coiled about an end region of a tubular UV lamp, and a straight portion positioned adjacent a middle region of the lamp, in order to accommodate the differential heat output of the lamp at the different regions thereof.

11 Claims, 3 Drawing Sheets

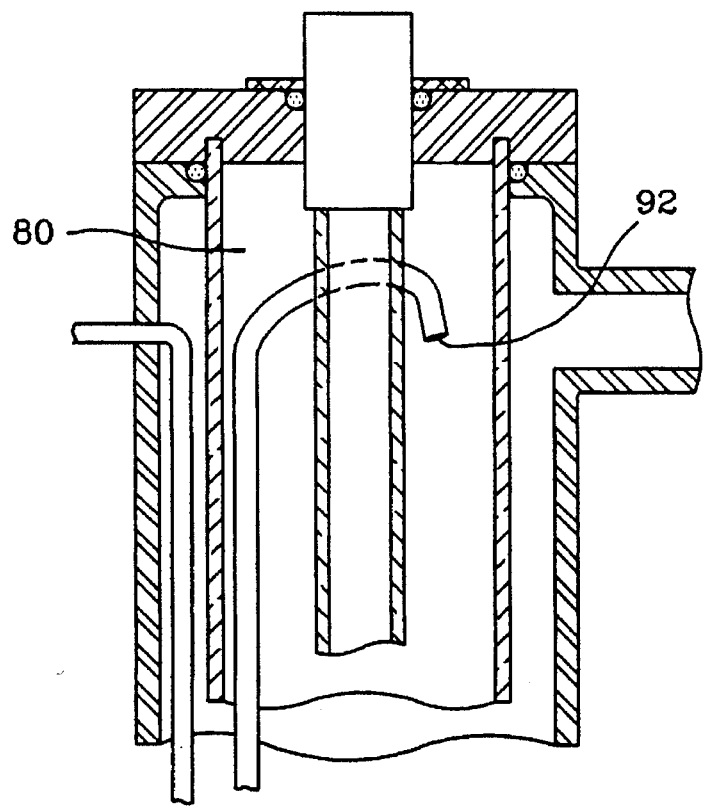
FIG 3
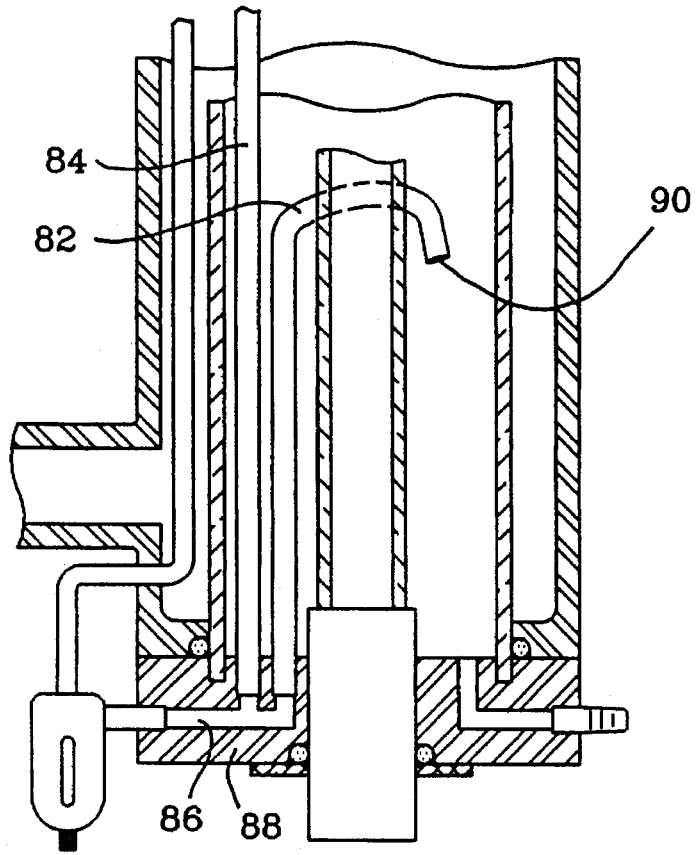

WATER DECONTAMINATING DEVICE

FIELD OF THE INVENTION

The present invention relates to a "dual mode" sterilizing apparatus for sterilizing water or other fluid contaminated with microbes or other contaminants. The term "dual mode" refers to the simultaneous generation of ionizing radiation and ozone within the apparatus, to provide a dual antimicrobial action.

BACKGROUND OF THE INVENTION

The antimicrobial uses of ozone and ionizing radiation, particularly ultraviolet ("UV") radiation, are well known for purifying water. Both agents are widely used to sterilize or purify water that is to be used for human consumption, and to purify effluent discharged from industrial processes. Other uses include the purification of recirculating water used in swimming pools and hot tubs, as well as the effluent of portable facilities, such as are found on boats. Due to the reactive nature of ozone, and to the volumes required for such uses, it is important that ozone be generated at or near the reaction chamber wherein the ozone is combined with the contaminated water. Accordingly, it is desirable to provide an efficient means for generating relatively large volumes of ozone with a relatively simple, inexpensive and compact apparatus.

It is understood that although reference is generally made herein to water as the contaminated medium, such devices may as well be used to treat other contaminated fluids.

Both single mode (i.e., employing UV or ozone alone as the sterilizing agent) and dual mode sterilizers have been in use for many years. Typically, a single mode device employs a UV tube to expose contaminated water to ionizing radiation, or exposes an air stream to UV radiation to generate ozone from the oxygen in the air, with the ozonated air then being mixed with the contaminated water. An old example of an ozone-producing apparatus is disclosed in U.S. Pat. No. 1,505,669 (Quain), wherein a UV lamp is positioned within an outer cylinder, with means for passing air between the tube and cylinder. The ionizing radiation emitted by the U.V. lamp reacts with the oxygen within the air passing by the tube, and ozonates the oxygen. The basic elements outlined in Quain are found, with various refinements, in virtually all ozone generators and dual mode sterilizers. See, for example U.S. Pat. Nos. 4,141,830 (Last); 4,179,616 (Coviello et al.); 4,189,363; and 4,230,571 (Dadd).

At its simplest, a dual mode sterilizer comprises: a) a UV lamp or other source of ionizing radiation enclosed within a chamber, within which a stream of oxygen-containing medium, usually air, is exposed to the radiation generated by the lamp; and b) a second chamber isolated from the first chamber, within which a stream of contaminated water flows and is therein exposed to radiation from the UV lamp. There may be provided means, either external to the device or incorporated therein, for combining the contaminated water with the ozonated air generated by the device.

In order to achieve maximum efficiencies in generating ozonated air, it is important that the air flowing past the ionizing element be relatively cool and dry. Various means have been employed to reduce the humidity in the air flowing through the device, including the provision of a desiccant-containing dryer (U.S. Pat. No. 4,230,571). This approach requires either regular replacement of the desiccant, or a means for continuously drying the desiccant to maintain effective functioning of the apparatus. It is desirable to provide a means for drying the air that doesn't require an external "active" air drying means or a desiccant. Preferably, the drying means requires little further energy consumption beyond that used in the other components of the apparatus, is relatively simple, and doesn't heat the air excessively.

A further drawback of present devices is that the UV lamp remains on at full force at all times during operation of the device, regardless of the flow of contaminated water through the device. This results in unnecessary heat buildup, shortened lamp life and increased power consumption in applications where flow rate varies. It is desirable to provide a means for reducing the lamp intensity as the flow rate through the device diminishes.

SUMMARY OF THE INVENTION

The present invention is intended to address the various drawbacks in existing systems as noted above, by providing a relatively efficient and simple sterilizing device that makes use of the temperature differential between the incoming contaminated water and the ambient air to dehumidify the air subsequently used for the generation of ozone. The invention takes advantage of the fact that in most instances, the temperature of the contaminated water (or other contaminated fluid) passing through the device will be lower than the ambient air temperature, and this temperature difference can be harnessed to remove moisture from the air.

The present invention consists of a dual mode sterilizing apparatus use in a system for sterilizing a fluid. The apparatus is adapted to simultaneously generate of ozone and expose a contaminated fluid to ionizing radiation. The apparatus comprises: a) a water chamber having an inlet and outlet, for the circulation of contaminated water; b) an air chamber for the circulation of an air supply; c) a UV lamp or other source of ionizing radiation positioned to expose the water within the water and air chambers to ionizing radiation; and d) an air supply conduit having an intake external to the apparatus and venting into the air chamber. The air supply conduit has a first part positioned within the water chamber, wherein the air is cooled by the relatively lower temperature of the water, and a second part positioned adjacent the UV lamp, where the air is slightly warmed by the proximity of the lamp. The second part may comprise a metal tube having a helical portion coiled about an end region of a tubular UV lamp, and a straight portion positioned adjacent a middle region of the lamp, in order to accommodate the differential heat output of the lamp at the different regions thereof. The cooling effect within the first part of the conduit causes moisture within the air to condense on the walls of the conduit. Means are preferably provided to collect the accumulated moisture following the condensation stage, for example with a water trap linked to the first part of the conduit. Within the second part of the conduit, the warming effect of the lamp causes the relative humidity of the air to drop, following which the air supply is vented into the air chamber for exposure to ionizing radiation. Following exposure to radiation from the lamp, the ozonated air is withdrawn through an outlet vent, for reaction with the water flowing through the system.

A three-stage filter, comprising felt, magnesium perchlorate and activated charcoal, may be provided to filter the air current before it enters the device.

BRIEF DESCRIPTION OF THE DRAWINGS

FIG. 3 is a side elevational view, in section, of a second embodiment of the device.

DETAILED DESCRIPTION OF THE PREFERRED EMBODIMENT

Figure 1:
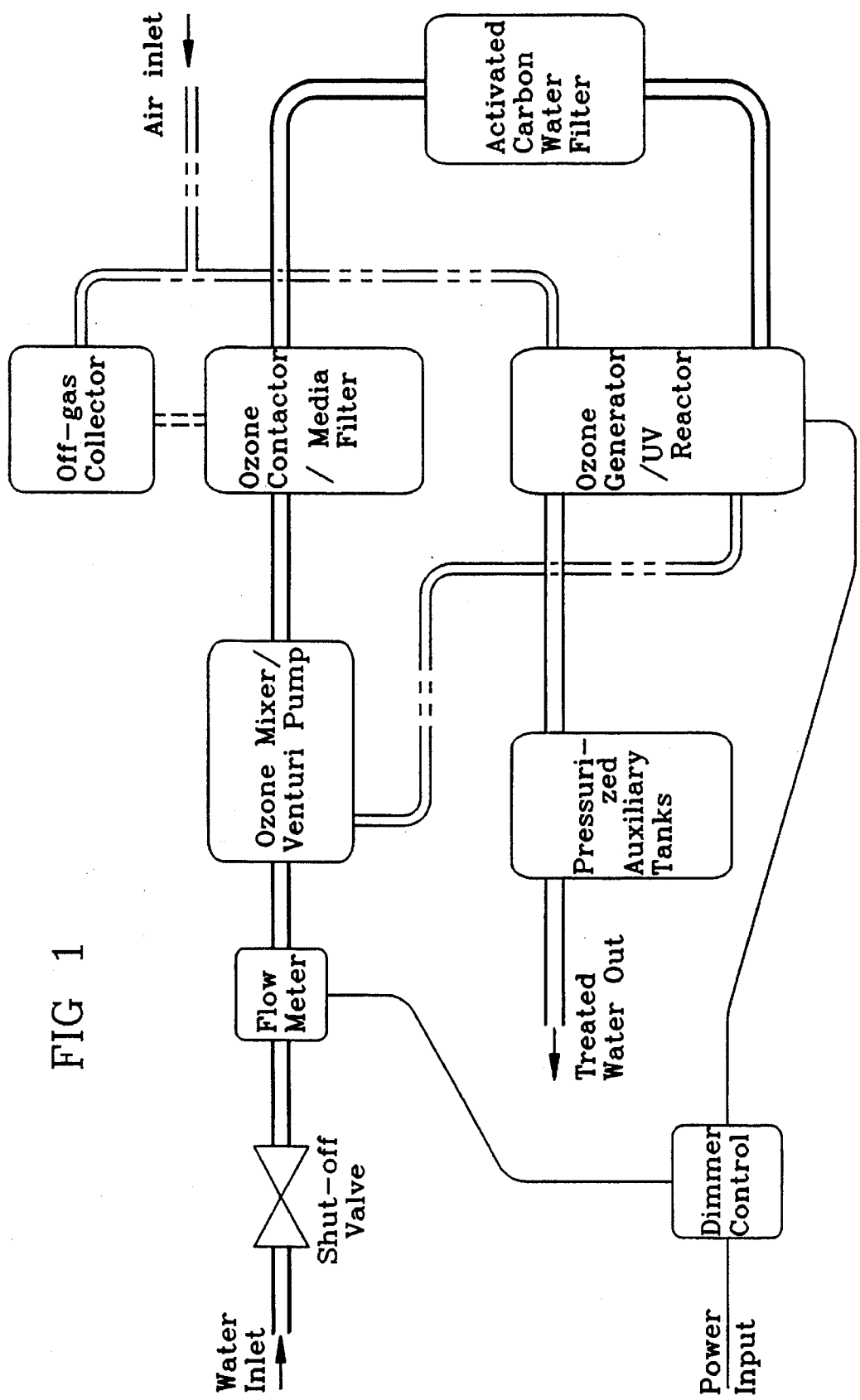
FIG. 1 is a schematic diagram of a sterilizing system incorporating the present invention.

The present invention is intended to comprise a component of a water decontamination system, as shown in FIG. 1, for the treatment of contaminated water with the antimicrobial activity of ozone and UV radiation. Water flowing into the system initially flows through a flowmeter, and then into an ozone mixer to perform an initial mixing of ozone-rich air and water. The ozone mixer includes a venturi pump, adapted to draw air through the ozone-generating component of the system. The water and ozonated air are then thoroughly reacted in an ozone contactor, with the spent gasses subsequently collected for recirculation. The water may then be further filtered, and then enters the dual-mode UV exposure chamber and ozone generator of the present invention. The now-treated water exits the system via an auxiliary holding tank provided to modulate water flow.

Figure 2:
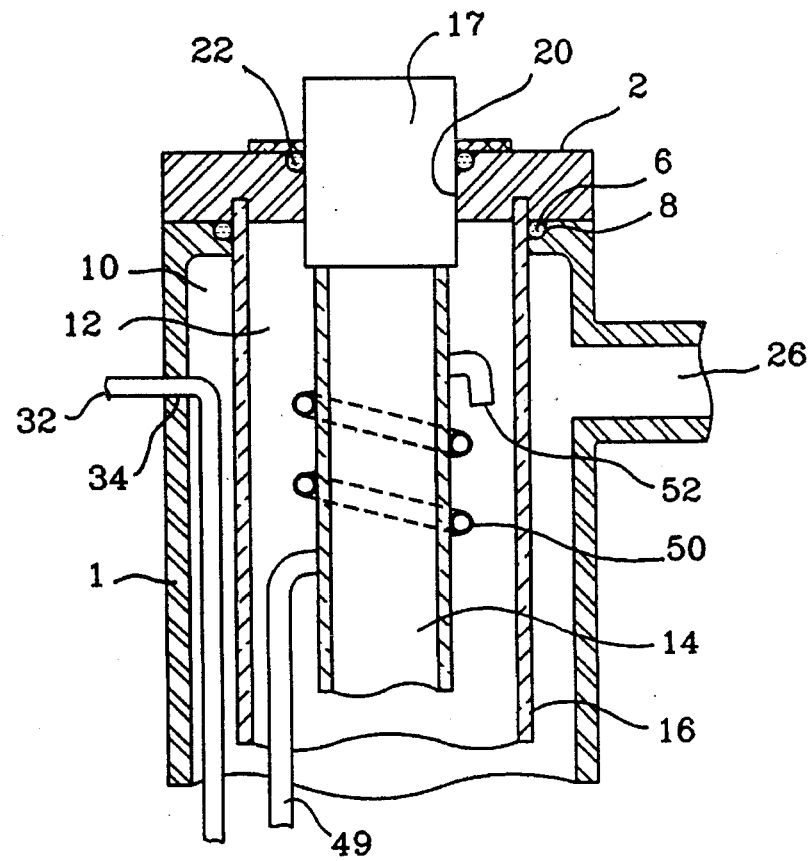
FIG. 2 is a side elevational view, in section, of a sterilizing apparatus according to the present invention.
Figure 2:
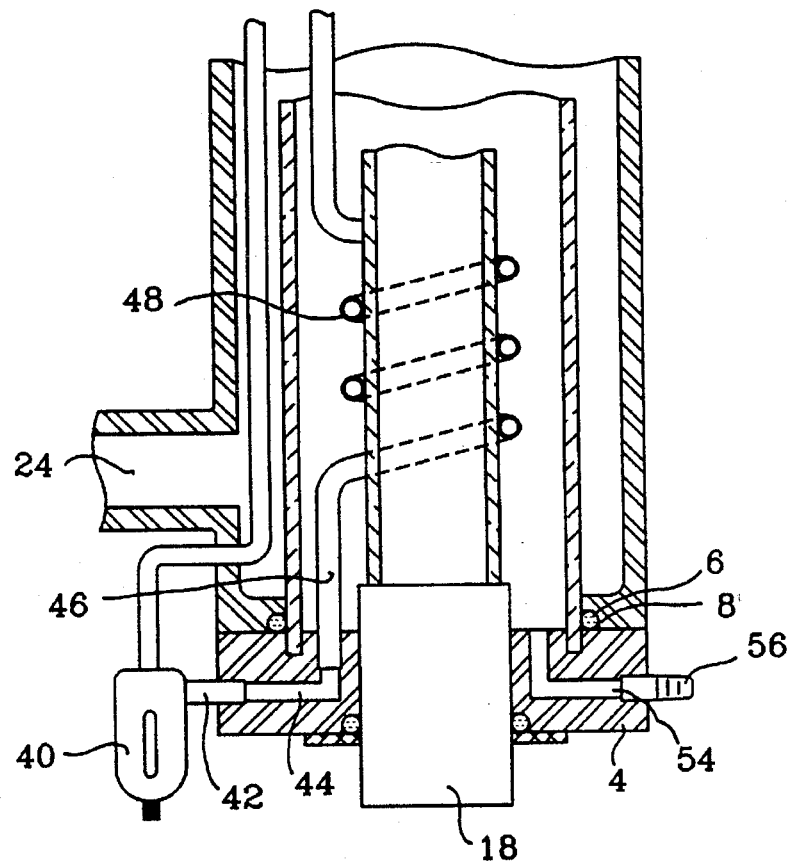

Referring to FIG. 2, the dual mode sterilizer according to the present invention is housed within a stainless steel cylindrical housing 1. The housing may be positioned with its longitudinal axis oriented vertically, although it will be understood that any orientation is possible. The directional references herein refer to the device in its usual vertical orientation. The ends of the housing 1 are sealed with upper and lower caps 2 and 4, respectively. The interior of the housing is divided into two concentric cylindrical chambers sealingly separated from each other by way of an o-ring seal 6 recessed into a shoulder 8 within each of the upper and lower caps 2 and 4. The chambers comprise an outer water jacket 10 and an inner air chamber 12. A cylindrical UV lamp 14 is positioned within the air chamber and extends the length thereof.

The wall 16 of the air chamber 12 is fabricated of quartz or other material transparent to UV radiation, in order to allow radiation from the UV lamp 14 to be transmitted into the water jacket for the sterilization of the water circulating therethrough. The top and bottom ends 17 and 18 of the UV lamp 14 extend through the upper and lower caps 2, 4, respectively, the lower end of the UV lamp having leads connected to a power source, not shown. The caps 2, 4 are each provided with an aperture 20 and an o-ring seal 22 to allow the ends of the lamp to extend through the caps without permitting the escape of air from the air chamber.

Contaminated water enters the water jacket 10 by way of entry pipe 24, extending horizontally from adjacent the lower end of the housing 1 and exits the chamber by way of exit pipe 26, positioned adjacent the upper end of the housing. The entry and exit pipes are linked to the decontamination system, as discussed above. The water current is driven through the device by the pressure thereof at the entry pipe 24. The required pressure may be generated by a pump, not shown, or by the system pressure of the water stream.

Production of ozone by the device is effected by exposing a current of air to the ionizing radiation produced by the UV lamp. The reaction of oxygen from the air with the radiation to produce ozone is well known and will not be described herein. The air current enters the system initially through a filter, shown schematically in FIG. 1, adapted to remove fine particulate matter from the incoming air. The filter is preferably a three-stage filter, comprising an initial felt filter, a secondary filter bed of activated charcoal, and a tertiary bed of magnesium perchlorate. A stainless steel tube 32 extends from the filter 30 and enters the housing 1 through an aperture 34 adjacent the upper end of the housing. Within the housing, the tube 32 extends vertically downwardly through the water jacket 10, and exits the housing adjacent the bottom end thereof below the water entry pipe 24. Moisture is removed from the air flowing downwardly through the tube as it contacts the walls of the tube cooled by contact with the contaminated water within the water jacket 10.

The lower end of the tube 32 is connected to a water trap 40 that collects water accumulating at the base of the tube. A second tube 42 exits the water trap and enters the housing again through the lower cap 4. A conduit 44 within the lower end cap accepts the second tube 42 and communicates with a desiccating tube 46 within the interior of the air chamber 12. The desiccating tube 46 extends upwardly through the inner chamber, the lower and upper portions thereof 48, 50 winding around the UV lamp. The middle portion 49 of the tube is straight, and extends parallel to the tube and spaced slightly apart therefrom. The air current passing through the desiccating tube 46 is warmed, and consequently its relative humidity lowered, by the heat generated by the UV lamp. The heat output of the middle portion of the UV lamp adjacent the middle portion 49 of the desiccating tube is greater than that of the end portions. Consequently, the end portions of the tube are coiled about the lamp to absorb a generally constant amount of heat from the lamp along the length thereof. The temperature of the air exiting the tube is, however, still below the ambient air temperature, in order to maintain the desired air temperature of somewhat below room temperature for optimal ozone production.

The upper end of the desiccating tube terminates in a nozzle 52, and the air current swirls downwardly through the interior of the air chamber 12, receiving exposure to UV radiation from the UV lamp, and exits the housing through a second aperture 54 within the lower end cap 4. The downward movement of the air current is assisted by the fact that as the oxygen within the air current becomes ozonated, it's weight increases. Consequently, the air at the bottom of the chamber will tend to have a higher concentration of ozone than at the top of the chamber.

The now ozonated air current is drawn from the second aperture 54, through an ozonated air conduit 56 linked to a venturi pump, shown schematically in FIG. 1, positioned within the water flow. The venturi pump serves as well to combine the ozonated air with the UV-exposed water exiting from the device, and may be linked with means for thoroughly combining and reacting the ozonated air with the water.

The intensity of the UV lamp is controlled by a dimmer linked to the UV lamp, shown schematically in FIG. 1. The dimmer is controlled by a flowmeter positioned at any point in the water stream. In FIG. 1, the flowmeter is shown as positioned adjacent the intake shut-off valve. The flowmeter provides an electrical signal increasing in strength as the water flow increases. The signal controls the dimmer. When the flow diminishes to zero, the dimmer shuts the UV lamp off. The flow required for maximal intensity of the lamp may be preset according to the strength of the lamp and the desired amount of UV exposure and ozone production for a given water flow.

A second embodiment of the device is illustrated in FIG. 3. In this embodiment, dual straight desiccating tubes are provided within the air chamber 80, extending vertically up the chamber. The first and second tubes 82, 84 exit a common conduit 86 within the lower end cap 88. The first tube has its exit nozzle 90 at about the midpoint of the air chamber 80, and the second tube has its exit nozzle 92 adjacent the top of the chamber. The combined cross-sectional area of the tubes 82, 84 is greater than the cross-sectional area of the common conduit, resulting in a pressure drop as the air enters the desiccating tubes. The expansion results in cooling of the air. The air within the first tube 82 experiences a greater degree of cooling than that within the second tube 84, from the relative rapidity of the pressure drop as compared with the longer tube 84. This relatively cooler air generates ozone more efficiently, and consequently less UV exposure time is required to generate an equivalent ozone content. As a result, the air descending from the nozzles of both tubes will have similar ozone contents upon exiting the chamber.

Although the present invention has been described by way of preferred embodiments thereof, it will be seen by those skilled in the art to which this invention relates that modifications and alternate variations may be made to the invention, without departing from the spirit and scope thereof as defined by the appended claims.

I claim:

1. A sterilizing apparatus for sterilizing a fluid, said apparatus comprising:
   a) a first chamber having an inlet and outlet, for the containment and circulation of said fluid;
   b) a second chamber sealingly isolated from the first chamber and having an inlet and outlet, for the containment of a gas stream;
   c) a source of ionizing radiation adapted to expose said first and second chambers to ionizing radiation for the simultaneous production of ozone within said second chamber and an antimicrobial action on said fluid within said first chamber;
   d) a gas conduit for conducting an oxygen-containing gas into said second chambers said gas conduit comprising first and second portions, said first portion being positioned within the first chamber, and comprising means for transferring heat from said gas to said fluid so as to cool said gas and condense moisture therefrom onto said conduit, said second portion being positioned within said second chamber adjacent said ionizing radiation source sufficiently close thereto to extract heat therefrom for the lowering of the relative humidity of said gas, said second portion terminating in said inlet into said second chamber.

2. An apparatus as claimed in claim 1 wherein said source of ionizing radiation is an ultraviolet lamp.

3. An apparatus as claimed in claim 1, wherein a portion of said conduit comprises a metal tube wrapped around said source for the transfer of heat from the source to the gas.

4. An apparatus as claimed in claim 3, wherein said tube comprises a helical portion coiled about an end region of said lamp, and a generally straight portion extending adjacent the middle region of said lamp.

5. An apparatus as claimed in claim 1 wherein said second chamber is positioned within said first chamber and a portion of the wall of the second chamber permits the passage of radiation therethrough into said first chamber.

6. An apparatus as claimed in claim 5 wherein said portion of the wall of the second chamber is fabricated from quartz.

7. An apparatus as claimed in claim 1 wherein there is further provided a filter for the removal of fine particulate matter from said gas prior to the entry thereof into said second chamber.

8. An apparatus as claimed in claim 7 wherein said filter comprises a three-stage filter, comprising an initial felt filter and filter beds containing activated charcoal and magnesium perchlorate.

9. An apparatus as claimed in claim 1 wherein there is further provided a venturi pump driven by the flow of fluid through said decontamination system, said pump adapted to draw said gas through the apparatus and combine it with the fluid subsequent to the ozonation of said gas.

10. An apparatus as claimed in claim 1, wherein said conduit includes first and second tubes each having an exit vent partway up said second chamber, said first tube having an exit vent higher than the exit vent of said second tube.

11. An apparatus as claimed in claim 10 wherein the cross-sectional area of said first and second tubes combined is greater than the cross-sectional area of the portion of the conduit positioned within the first chamber.

* * * * *